United States Patent
Gama De Abreu et al.

(10) Patent No.: US 6,394,962 B1
(45) Date of Patent: May 28, 2002

(54) ARRANGEMENT FOR THE DETERMINATION OF THE EFFECTIVE PULMONARY BLOOD FLOW

(75) Inventors: Marcelo Gama De Abreu; Detlev Michael Albrecht, both of Dresden (DE)

(73) Assignee: Technische Universitaet Dresden, Dresden (DE)

( * ) Notice: Subject to any disclaimer, the term of this patent is extended or adjusted under 35 U.S.C. 154(b) by 0 days.

(21) Appl. No.: 09/638,996

(22) Filed: Aug. 14, 2000

Related U.S. Application Data

(63) Continuation of application No. 09/269,458, filed as application No. PCT/DE97/02194 on Sep. 26, 1997, now Pat. No. 6,106,480.

(30) Foreign Application Priority Data

Sep. 28, 1996 (DE) .......................................... 196 40 152
Sep. 24, 1997 (DE) .......................................... 197 42 226

(51) Int. Cl.⁷ .............................................. A61B 5/08
(52) U.S. Cl. ...................................... 600/529; 600/532
(58) Field of Search .................................. 600/529, 532

(56) References Cited

U.S. PATENT DOCUMENTS 5,005,582 A * 4/1991 Serikov et al. ............. 600/532
5,299,579 A * 4/1994 Gedeon et al. ............. 600/532

* cited by examiner

Primary Examiner—Kevin Shaver
Assistant Examiner—Navin Natnithithadha
(74) Attorney, Agent, or Firm—Jordan and Hamburg LLP

(57) ABSTRACT

The invention relates to a device to determine effective pulmonary blood flow (PBF) by means of partial $CO_2$ rebreathing. The device is characterized in that it comprises an endotracheal tube whose conduit leading from the patient to the respirator is divided up into two lanes between a controllable three-way valve (4) and a Y-piece; one lane builds a larger dead area (6) for $CO_2$ rebreathing whereby, in order to measure $CO_2$ elimination and end expiratory partial $CO_2$ pressure a $CO_2$ sensor (3) and a respiration flow sensor (1) are provided on the endotracheal tube of the patient. The calculation of effective pulmonary blood flow is provided by a microprocessor/controller (7) which also controls the three-way valve (4) which provides the switching between both lanes.

6 Claims, 2 Drawing Sheets

ARRANGEMENT FOR THE DETERMINATION OF THE EFFECTIVE PULMONARY BLOOD FLOW

REFERENCE TO RELATED APPLICATION

Figure 1:
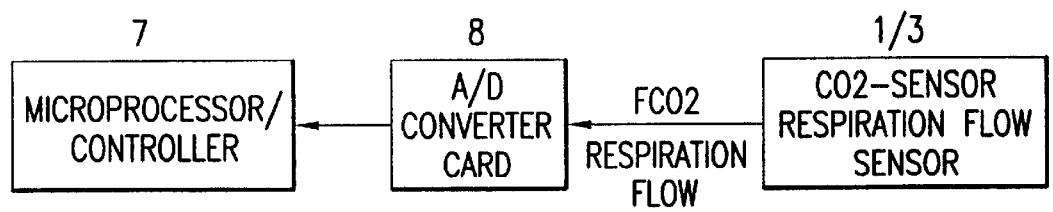

This is a continuation of application Ser. No. 09/269,458, filed Apr. 23, 1999, now U.S. Pat. No. 6,106,480.

Arrangement for the Determination of the Effective Pulmonary Blood Flow

The invention relates to an arrangement for the determination of the effective pulmonary blood flow according to the generic part of claim 1.

From the paper Steinhart, C. M., Burch, K. D., Bruno, S., Parker, D. H.: Noninvasive determination of effective (nonshunted) pulmonary blood flow in normal and injured lungs, Crit. Care Med., 1989, Vol. 17, No. 4, pp. 349–353 the Multiple-Inert-Gas method with rebreathing of helium, acetylene and carbon monoxide in oxygen and nitrogen from a respiratory bag is known. A disadvantage of this measurement is the relatively great effort to nitrogen from a respiratory bag is known. A disadvantage of this measurement is the relatively great effort to prepare the gas mixtures for rebreathing, the demand for special measuring instruments that can measure the concentrations of gases in the breathed air or the breathing flow, respectively, and the necessity of a person to connect the respiratory bag to the patient and maintain it. For those reasons the measurement of the effective pulmonary blood flow can only be executed by specialists and is for research purposes in almost all cases.

Further, from the paper by Inman, M. D., Hughson, R. L., and Jones, N. L.: Comparison of cardiac output during exercise by single-breath and $CO_2$ rebreathing methods, J. Appl. Physiol., Vol. 58, pp. 1372–1377, 1985, the total $CO_2$ rebreathing method and the so-called single-breath method are known. Disadvantages of these methods are distinct increases of $CO_2$ pressure in the arterial blood, as the $CO_2$ elimination is interrupted, and the impeding of the respiration. Other disadvantages are those of the Multiple-Inert-Gas method, namely the preparation of gas mixtures for rebreathing having certain $CO_2$ concentrations, the demand for special measuring instruments that can measure the concentrations of gases in the breathed air or the breathing flow, respectively, and the necessity of a person to connect the respiratory bag to the patient and maintain it.

Another method known is a partial $CO_2$ rebreathing method (according to Gedeon, A., Forslund, L., Hedenstierna, G. and Romano, E.: A new method for noninvasive beside determination of pulmonary blood flow, Med. & Biol. Eng. & Comp., 1980, Vol. 18, pp. 411–418) based on varying minute ventilation. Disadvantage of this method is the variation of the mean respiratory tract pressure and of the pressure at the end of expiration. Due to this variation of the respiratory tract pressure the pulmonary blood flow also varies and both the medical stability of the lungs and the gas exchange are impeded.

From the paper by Capek, J. M. and Roy, R. J.: Noninvasive measurement of cardiac output using partial $CO_2$ rebreathing; IEEE Transactions on Biomedical Engineering, 1988, Vol. 35, No. 9, pp. 653–661) the partial $CO_2$ rebreathing method with change of the dead space of the apparatus is known, which is performed using a mass spectrometer and special respiratory flow sensors at the endotracheal tube and can measure the total cardiac output. The change between two different dead spaces is performed by a PC-controlled electromagnetic valve. The partial expiration termination pressure and the $CO_2$ elimination are determined for the respiration by both dead spaces. The $CO_2$ partial pressure at the end of expiration is converted to the arterial $CO_2$ concentration and the total cardiac output can be calculated from the division of the $CO_2$ elimination difference by the arterial $CO_2$ concentration difference. A disadvantage of this method is the demand for apparatus for the measurement of the $CO_2$ concentration in the breathed air (mass spectrometer) and of the respiratory flow at the endotracheal tube (Fleisch pneumatocograph).

It is the objective of this invention to describe a clinically practicable arrangement for noninvasive determination of the effective pulmonary blood flow whereby the effective pulmonary blood flow is the cardiac output minus the intrapulmonary shunt proportion. Only that portion of the cardiac output is intended to be determined which is available for gas exchange. This arrangement requires only little apparatus, does not essentially influence the respiratory schedule, and is capable of being automated.

According to the invention, the problem is solved using features given by claim 1. The dependant subclaims give other useful developments and embodiments.

The selected parameters, above all, made it possible for the first time to determine the effective pulmonary blood flow during respiration, i.e. only that portion of the cardiac output that is available for gas exchange.

Figure 2:
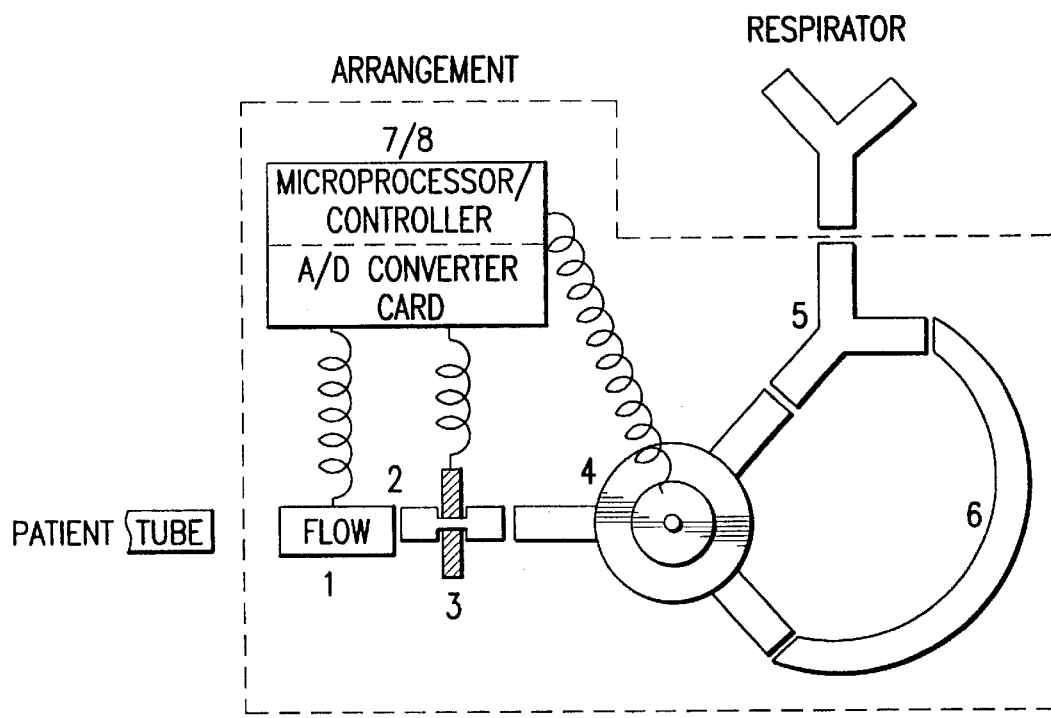

The arrangement according to the invention, which is controlled by a microprocessor or a controller, the signals of a main stream $CO_2$ sensor and a respiratory flow sensor are detected. The main stream $CO_2$ sensor is intended for measurement of the $CO_2$ concentration of the respiratory air, the respiratory flow sensor for measurement of the respiratory flow (FIG. 1). The respiratory flow sensor is located between the endotracheal tube and the $CO_2$ sensor. There is a controllable 3-way valve between the endotracheal tube and the Y-fitting of the respirator. This valve is switched by the microprocessor or the controller so that the patient is respirated through a short or a long branch (so-called dead space) (FIG. 2).

Measurements of the $CO_2$ elimination and expiration termination $CO_2$ partial pressure are first performed during respiration through the small dead space. This period lasts approx. 60 s, and is called non-rebreathing period. After this period during an inspiratory cycle the 3-way valve is switched so that the patient is respirated through the bigger dead space (long branch) and rebreathes a gas mixture that consists of his or her own expired air and fresh air from the respirator. Thus no separate $CO_2$ source for rebreathing is required. The time for switching the 3-way valve is derived from the absence of $CO_2$ in the inspiratory air. This causes no essential variation of the respiratory pressure. The subsequent period last approx. 30 s is called rebreathing period. The $CO_2$ elimination and the expiration termination $CO_2$ partial pressure of this period are measured as mean values of each variable during a plateau that forms in the range of 15 to 30 s during this period (second half).

The arrangement according to the invention creates the possibility to set the respiratory schedule of the patient in the respirator such that the maximum pulmonary blood flow is achieved with the lowest mean and expiration termination respiratory tract pressure. This lowers the risk of the patient to suffer from a barotrauma, i.e. lung damage due to increased airway pressure is avoided and, simultaneously, the oxygen supply to the organs is optimised. This solution also raises the possibility to monitor the haemodynamics of the patient noninvasively and to record it automatedly. If simultaneous measurements of the cardiac output are taken, the found solution makes it possible to measure the percentage of the non-breathed cardiac output (so-called intrapulmonary shunt) without the inspiratory oxygen concentration being increased and blood samples being required.

Figure 3:
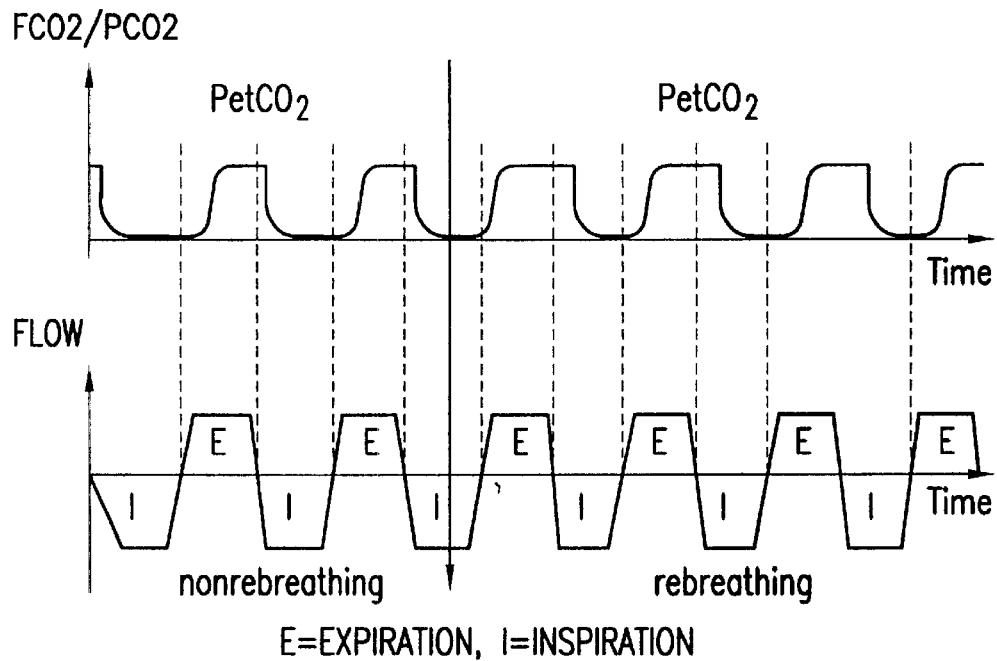
Figure 4:
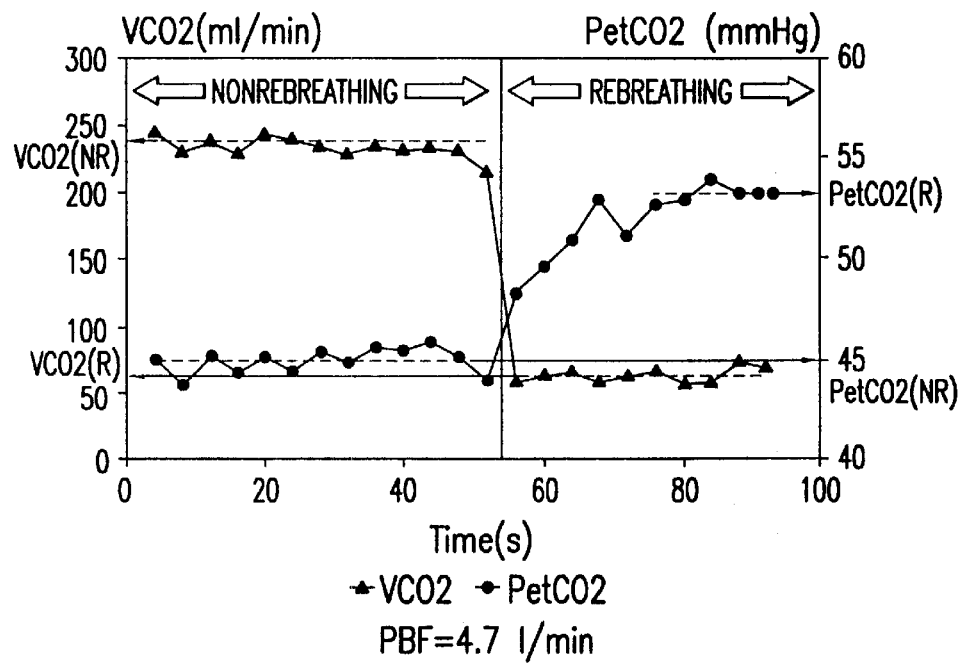

In the following, further details of the arrangement will be disclosed. By means of the accompanying drawings it is shown by:

FIG. 1 an arrangement of a microprocessor or a controller for the measurement of the effective pulmonary blood flow FIG. 2 an arrangement according to the invention with a microprocessor/controller and respirator FIG. 3 an example of a $CO_2$ concentration and respiratory flow plot taken with the arrangement according to the invention FIG. 4 an example of an expiration termination $CO_2$ partial pressure and $CO_2$ elimination plot together with the calculated pulmonary blood flow.

In FIG. 1, an arrangement of a microprocessor/controller for the measurement of the effective pulmonary blood flow that consists of four components is presented. The various components are connected with each other through cable and plug. According to FIG. 1 the system includes a microprocessor/controller 7 and an analog-digital-converter card 8 that registers and processes the $CO_2$ concentration and respiratory flow signals from the $CO_2$ sensor 3 or respiratory sensor 1, respectively.

In FIG. 2, a microprocessor- or controller-controlled arrangement for the measurement of the effective pulmonary blood flow is presented that consists of seven components, or less or more as desired. According to FIG. 2 the endotracheal tube of the patient is connected to one side of the respiratory flow sensor 1. To the other side of the respiratory flow sensor 1, a $CO_2$ cuvet 2 is connected. A $CO_2$ sensor 3 is inserted into the $CO_2$ cuvet 2. A switchable 3-way valve 4 is connected to the other side of the $CO_2$ cuvet 2. One of the outputs of the 3-way valve 4 is connected to a Y-fitting 5, the other output is connected to the dead space 6 for rebreathing. A respirator and the dead space 6 for rebreathing are also connected to the Y-fitting 5. The dead space 6 for rebreathing is about 200 ml, or less or more as desired, depending on the respiratory schedule of the patient. A connection exists to the 3-way valve 4, through which the inner diaphragm of the valve 4 can be moved by pressure or flow. The microprocessor/controller 7 controls the 3-way valve 4, and senses and processes the $CO_2$ concentration and respiratory flow signals.

In FIG. 3, the curves of the $CO_2$ concentration in the respiratory air and of the respiratory flow during a measurement are presented. In the expiration period $CO_2$ is expired through the endotracheal tube. The $CO_2$ concentration ($FCO_2$) of the expired air, which corresponds with the $CO_2$ partial pressure ($PCO_2$) of the air, increases with the expired volume and reaches a maximum at the end of expiration. The $CO_2$ partial pressure at this time, the so-called expiration termination $CO_2$ partial pressure ($PetCO_2$), approximately corresponds with the $CO_2$ partial pressure in the ventilated pulmonary capillaries. During the nonrebreathing period $PetCO_2$ values are measured that only just differ. During the rebreathing period part of the expired $CO_2$ is rebreathed. Therefore the behaviour of the $CO_2$ partial pressure in the breathing air modifies and $PetCO_2$ increases.

In FIG. 4, the curves of the expiration termination $CO_2$ partial pressure corresponding with the maximum of the $CO_2$ concentration during expiration and of the $CO_2$ elimination per respiration during measurement using the arrangement according to the invention are given. The $CO_2$ elimination decreases during a partial $CO_2$ rebreathing and the expiration termination $CO_2$ partial pressure increases until a plateau has been reached, usually after approx. 15 s. The effective pulmonary blood flow is calculated from the four parameters given in FIG. 4, following the equation:

$$PBF = \frac{(VCO_2(NR) - VCO_2(R))}{f(PetCO_2(R), PetCO_2(NR), Hb) \times Fs}$$

$VCO_2(NR)$ is meant to be the $CO_2$ elimination, in ml/min, during the nonrebreathing period measured as the mean value of the $CO_2$ elimination of complete respirations within 60 s until immediately before the beginning of the rebreathing period. The $CO_2$ elimination of one respiration is calculated from the product of the respiratory flow (ml/min) and $CO_2$ concentration over time. $PetCO_2(R)$ is the expiration termination $CO_2$ partial pressure, in mmHg, in the respiratory air during the nonrebreathing period measured as the mean value of expiration termination $CO_2$ partial pressures of complete respirations within 60 s until immediately before the beginning of the rebreathing period.

$PetCO_2(NR)$ is the expiration termination $CO_2$ partial pressure, in mmHg, in the respiratory air during the rebreathing period measured as the mean value of the expiration termination $CO_2$ partial pressures of complete respirations within 60 s until immediately before the beginning of the rebreathing period.

$VCO_2(R)$ is the $CO_2$ elimination, in ml/min, during the rebreathing period measured as the mean value of the $CO_2$ elimination of complete respirations within 15 to 30 s after the patient has begun to be respired through the big dead space 6, i.e. after switching of the 3-way valve 4 into the rebreathing position. The $CO_2$ elimination of one respiration is calculated from the product of the respiratory flow, in ml/min, and the $CO_2$ concentration, in %, over time.

$PetCO_2(R)$ is the expiration termination $CO_2$ partial pressure, in mmHg, in the respiratory air during the rebreathing period measured as the mean value of the expiration termination $CO_2$ partial pressures of complete respirations within 15 to 30 s after the patient has begun to be respired through the big dead space 6 (after switching of the 3-way value 4 into the rebreathing position).

Finally, the function $f(PetCO_2(R), PetCO_2(NR), Hb)$ is the standardised $CO_2$ dissociation curve in blood. By this function which has already been described in the literature (McHardy, G. J. R.: The relationship between the differences in pressure and concentration in arterial and venous blood, Cli. Sci., 1967 32, pp. 299–309), from the $PetCO_2(R)$ and $PetCO_2(NR)$ values and using also the baemoglobin concentration (Hb, g/dl), which has to be determined with a different device in a blood sample of the patient, the difference of the $CO_2$ concentrations ($\Delta CCO_2$, % by volume—ml/100 ml of blood) in the pulmonary capillary blood between the rebreathing and nonrebreathing periods is calculated using the following equation:

$f(PetCO_2(R), PetCO_2(NR), Hb) = \Delta CCCO_2 = 11,02 \times (PetCO_2(R)^{0,396} - PetCO_2(NR)^{0,396}) - 0,015 \times (15 - Hb) \times (PetCO_2(R) - PetCO_2(NR))$ Further, Fs is a scale factor for the representation of the effective pulmonary blood flow, in l/min. Fs is defined to be 10.

From the calculation the effective pulmonary blood flow, PBF, in l/min, is obtained.

What is claimed is:

1. Arrangement for the determination of the effective pulmonary blood flow by means of partial $CO_2$ rebreathing characterized in that the line from the endotracheal tube of the patient (tube) to the respirator between a controllable 3-way valve (4) and a Y-fitting (5) is split into two branches, one branch forms a bigger dead space (6) for the $CO_2$ rebreathing whereby for measurement of the $CO_2$ elimination and expiration termination $CO_2$ partial pressure a $CO_2$ sensor (3) and a respiratory flow sensor (1) at the endotracheal tube of the patient and for calculation of the effective pulmonary blood flow a microprocessor/controller (7) is provided, the switching between the two branches is carried out by the 3-way valve (4) that can be controlled through the microprocessor/controller (7), the calculation of the effective pulmonary blood flow is performed using the equation $$PBF = \frac{(VCO_2(NR) - VCO_2(R))}{f(PetCO_2(R), PetCO_2(NR), Hb) \times Fs},$$

whereby $VCO_2(NR)$ is the $CO_2$ elimination (ml/min) during the nonrebreathing period measured as the mean value of the $CO_2$ elimination of complete respirations within 60 s until immediately before the beginning of the rebreathing period, $PetCO_2(NR)$ is the expiration termination $CO_2$ partial pressure (mmHg) in the respiratory air during the rebreathing period measured as the mean value of the expiration termination $CO_2$ partial pressures of complete respirations within 60 s until immediately before the beginning of the rebreathing period, $VCO_2(R)$ is the $CO_2$ elimination (ml/min) during the rebreathing period measured as the mean value of the $CO_2$ elimination of complete respirations within 15 to 30 s after the patient has begun to be respired through the big dead space (6) (after switching the 3-way valve (4) into the rebreathing position), $PetCO_2(R)$ is the expiration termination $CO_2$ partial pressure (mmHg) in the respiratory air during the rebreathing period measured as the mean value of the expiration termination $CO_2$ partial pressures of complete respirations within 15 to 30 s after the patient has begun to be respired through the big dead space (6) (after switching the 3-way value (4) into the rebreathing position), Fs is a scale factor for the representation of the effective pulmonary blood flow in l/min with Fs=10, PBF is the effective pulmonary blood flow (l/min) whereby $f(PetCO_2(R), PetCO_2(NR), Hb)$ is the standardised $CO_2$ dissociation curve in blood and is calculated by inserting the measured values into the equation $$f(PetCO_2(R), PetCO_2(NR), Hb) = \Delta CCO_2 = 11{,}02 \times (PetCO_2(R)^{0,396} - PetCO_2(NR)^{0,396}) - 0{,}015 \times (15 - Hb) \times (PetCO_2(R) - PetCO_2(NR)).$$

2. Arrangement to claim 1 characterized in that the volume of the dead space (6) is 100, 200, 300, 400 or 500 ml.

3. Arrangement to claim 1 or 2 characterized in that the respiratory flow sensor (1) is inserted into the line at the endotracheal tube of the patient (tube).

4. Arrangement to claim 1 or 2 characterized in that the $CO_2$ sensor (3) is an infrared sensor.

5. Arrangement to claim 4 characterized in that the infrared sensor is positioned in a $CO_2$(2) cuvet.

6. Arrangement to any of claims 1 or 2 characterized in that the dead space (6) is an exchangeable tube or cylinder.

* * * * *